United States Patent
DeSellem et al.

(10) Patent No.: US 10,415,825 B2
(45) Date of Patent: Sep. 17, 2019

(54) METHODS OF GENERATING ENERGY FROM CELLULOSIC BIOFUEL WASTE

(71) Applicant: THE BABCOCK & WILCOX COMPANY, Barberton, OH (US)

(72) Inventors: James F DeSellem, Salineville, OH (US); Thomas J Flynn, North Canton, OH (US); Karl M Heil, North Canton, OH (US); Eric L Wells, Massillon, OH (US)

(73) Assignee: The Babcock & Wilcox Company, Barberton, OH (US)

( * ) Notice: Subject to any disclaimer, the term of this patent is extended or adjusted under 35 U.S.C. 154(b) by 173 days.

(21) Appl. No.: 15/601,230

(22) Filed: May 22, 2017

(65) Prior Publication Data
US 2017/0350593 A1   Dec. 7, 2017

Related U.S. Application Data (60) Provisional application No. 62/346,625, filed on Jun. 7, 2016.

(51) Int. Cl.

| | |
|---|---|
| *F23G 5/30* | (2006.01) |
| *C08L 97/00* | (2006.01) |
| *C08L 97/02* | (2006.01) |
| *C12P 7/06* | (2006.01) |
| *F23C 10/04* | (2006.01) |
| *F23G 5/12* | (2006.01) |

(Continued)

(52) U.S. Cl.
CPC ............... *F23G 5/30* (2013.01); *C08L 97/005* (2013.01); *C08L 97/02* (2013.01); *C12P 7/06* (2013.01); *F23C 10/04* (2013.01); *F23C 10/22* (2013.01); *F23G 5/12* (2013.01); *C10L 5/445* (2013.01); *C10L 2200/04* (2013.01); *C10L 2200/0469* (2013.01); *C10L 2290/02* (2013.01); *C10L 2290/06* (2013.01); *C12P 7/10* (2013.01); *F23C 2206/102* (2013.01); *F23G 2209/12* (2013.01); *F23G 2209/26* (2013.01); *F23G 2900/50007* (2013.01); *Y02E 20/12* (2013.01); *Y02E 50/16* (2013.01); *Y02E 50/17* (2013.01); *Y02P 20/136* (2015.11)

(58) Field of Classification Search
CPC ....................................................... F23G 5/30
See application file for complete search history.

(56) References Cited

U.S. PATENT DOCUMENTS

| | | | | |
|---|---|---|---|---|
| 4,335,683 A | * | 6/1982 | Criswell | ............. F22B 31/0076 110/101 CF |
| 4,960,057 A | * | 10/1990 | Ohshita | ................... B01J 8/1872 110/245 |

(Continued)

FOREIGN PATENT DOCUMENTS

EP    0286845 A1 * 10/1988    ............ F22B 31/003

OTHER PUBLICATIONS

EP0286845A1—machine translation (Year: 1988).*

*Primary Examiner* — Nathaniel Herzfeld
(74) *Attorney, Agent, or Firm* — Michael J. Seymour (57) ABSTRACT

Energy is generated from cellulosic biofuel waste streams, specifically a lignin filter cake and a waste syrup, by combusting these waste products in a fluidized bed combustor under specified conditions. The heat and steam generated can be used to generate electricity and/or in cellulosic biofuel production processes.

20 Claims, 7 Drawing Sheets

(51) Int. Cl.
*F23C 10/22* (2006.01)
*C12P 7/10* (2006.01)
*C10L 5/44* (2006.01)

(56) References Cited

U.S. PATENT DOCUMENTS

| | | | | |
|---|---|---|---|---|
| 2005/0274308 | A1* | 12/2005 | Copeland | F23C 10/30 |
| | | | | 110/346 |
| 2010/0325942 | A1* | 12/2010 | Eriksson | C10L 1/322 |
| | | | | 44/307 |
| 2011/0259284 | A1* | 10/2011 | Rantee | F22B 31/0007 |
| | | | | 122/22 |
| 2014/0102342 | A1* | 4/2014 | Maryamchik | F22B 31/0038 |
| | | | | 110/245 |
| 2014/0305357 | A1* | 10/2014 | DeSellem | F23C 1/10 |
| | | | | 110/347 |
| 2015/0101242 | A1* | 4/2015 | Hill | C05D 9/00 |
| | | | | 44/556 |
| 2015/0101511 | A1* | 4/2015 | Deruyter | C10L 5/445 |
| | | | | 106/705 |
| 2015/0122161 | A1* | 5/2015 | Landon | C10L 9/10 |
| | | | | 110/342 |
| 2016/0084498 | A1* | 3/2016 | Geraets | F23G 5/30 |
| | | | | 110/348 |

* cited by examiner

METHODS OF GENERATING ENERGY FROM CELLULOSIC BIOFUEL WASTE

BACKGROUND

The present disclosure relates to the use of waste streams to generate energy. In particular, waste streams formed by the production of cellulosic ethanol are used herein. The disclosure also relates to fluidized-bed boilers, such as a bubbling fluidized-bed (BFB) or circulating fluidized-bed (CFB) boiler, for combusting such products and materials, and to related arts.

During combustion, the chemical energy in a fuel is converted to thermal heat inside the furnace of a boiler. The thermal heat is captured through heat-absorbing surfaces in the boiler to produce steam. Fuels used in the furnace include a wide range of solid, liquid, and gaseous substances. Combustion transforms the fuel into a large number of chemical compounds. In some applications, solid biomass waste byproducts are used as fuel for the fluidized-bed boiler.

Fluidized-bed boilers are one way to burn solid fuels. Generally speaking, a fluidized-bed boiler includes a bed formed from a stacked height of solid particles. A fluidization gas distribution grid, such as an open bottom system or a flat floor system, is located beneath the bed. An open-bottom system is characterized by widely spaced distribution ducts on which are mounted air bubble caps for distributing fluidizing gas (typically air) under pressure to fluidize the bed of solid particles. In a flat floor system, the distribution ducts form the floor of the boiler. At sufficient gas velocities, the solid particles exhibit liquid-like properties.

Figure 1:
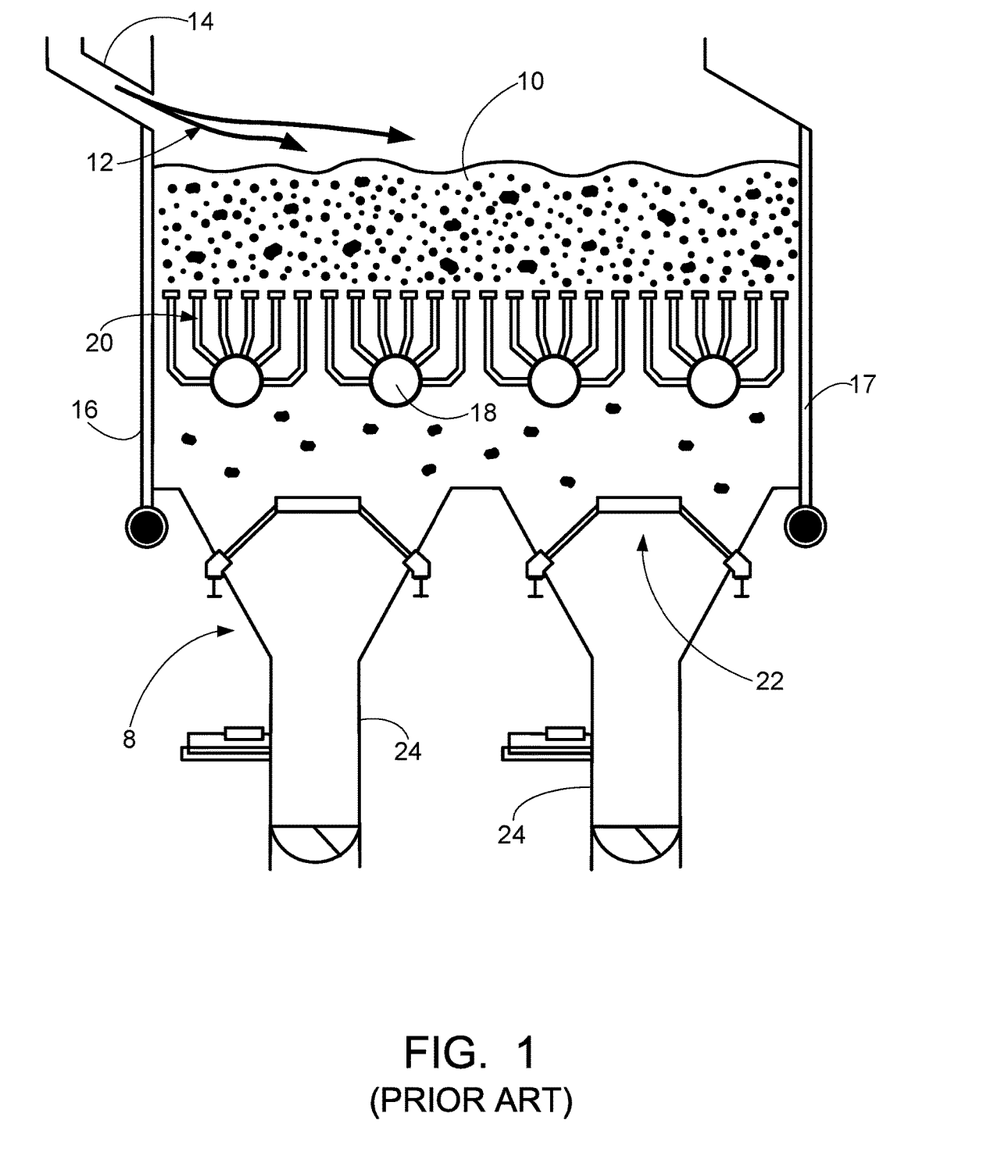
FIG. 1 diagrammatically shows an illustrative bubbling fluidized-bed (BFB) boiler of a known design.

With reference to FIG. 1, an illustrative bubbling fluidized-bed (BFB) boiler 8 of a known design (available from The Babcock & Wilcox Company, Barberton, Ohio, USA) includes a bubbling bed 10 onto which fuel 12 is delivered via a feeder 14. The fluidized bed 10 suitably comprises solid particles such as, for example, sand. A gas-tight furnace flue (only the lower portion of which is shown in FIG. 1) includes gas-tight tube walls 16, 17 made up of tubes through which water flows to cool the walls. A fluidizing gas, such as air, is introduced into the bubbling bed 10 through ducts 18, and spaced-apart bubble caps 20 facilitate removal of large tramp material. In an underbed ash removal system 22, tramp material moves downward and cools before being removed through bottom hoppers 24 onto a suitable conveyor system or the like (not shown). Heat from combustion on the fluidized bed 10 heats water in the wall tubes 16, 17 which may drive a steam generator or other useful work. In some embodiments, water in the tube walls 16, 17 flows in a closed-loop recirculation path (usually including a make-up water line). The feeder 14 may pass through a non-water-cooled refractory furnace wall (e.g., a brick furnace wall) rather than through tube wall 16 as in the illustrative embodiment of FIG. 1, or through any other type of boiler wall. It is contemplated for the furnace wall through which the feeder 14 passes to include additional features such as thermal insulation material, an outer casing, or so forth.

Cellulosic ethanol is an advanced type of biofuel produced from wood, grasses, or the inedible parts of plants. This type of biofuel is produced from lignocellulose, a structural material that comprises much of the mass of plants. Lignocellulose is composed mainly of cellulose, hemicellulose and lignin. Corn stover, switchgrass, miscanthus grass, wood chips, agricultural residue, and even the byproducts of lawn and tree maintenance are some of the feedstock containing lignocellulose.

The production of cellulosic ethanol biofuel typically requires additional processing with specialty chemicals, enzymes, and microorganisms to break down the lignocellulose. As a result, the waste products of cellulosic ethanol production are significantly different from those of the traditional starch ethanol process, which primarily uses cereal grains (e.g. corn kernels) as the feedstock. There are typically two waste streams from the cellulosic ethanol biofuel process. One is a lignin filter cake (cake) with a typical moisture range of 35% to 60% and remainder solids. The second is a syrup with a typical moisture range of 30% to 50% and remainder solids.

Unlike the waste products of starch ethanol production, the waste products from the cellulosic ethanol biofuel process typically cannot be sold as either feed or fertilizer due to the chemistry of the waste products resulting from the specialty mixture of chemicals, enzymes, and microorganisms needed to produce this biofuel. It would be desirable to provide methods and devices that can be used to derive the useful energy contained in the cellulosic ethanol waste products.

BRIEF DESCRIPTION

The present disclosure thus relates to methods of generating energy from cellulosic ethanol biofuel waste, and to the boilers/systems that can be used to practice those methods. The lignin filter cake and the waste syrup are fed into a fluidized-bed boiler, which is operated so as to combust these waste products and generate energy. That energy may be in the form of heated gas, steam, or electricity. The energy can be used to power the cellulosic ethanol production processes or other processes.

Disclosed herein are various methods for generating energy from cellulosic ethanol biofuel waste, comprising: feeding a lignin filter cake to a fluidized bed; feeding a waste syrup to the fluidized bed; and combusting the lignin filter cake and the waste syrup to generate energy.

The lignin filter cake may have a moisture content of about 35% to about 60%. The waste syrup may have a moisture content of about 30% to about 50%.

In particular embodiments, the waste syrup is fed as a stream or multiple streams directed at the plan area of the fluidized bed, and more particularly the center of the plan area. The waste syrup is generally fed to the fluidized bed at a temperature of about 100° F. to about 200° F. The waste syrup can be fed separately from any solids lignin filter cake) so as to minimize agglomeration.

The fluidized bed may have a bed temperature of about 1200° F. to about 1500° F. In some embodiments, the flue gas generated by the fluidized bed is recirculated back to the fluidized bed. In particular embodiments, the furnace wall temperature is kept at about 1000° F. or less.

In additional embodiments, an additive can be introduced to the waste syrup to reduce agglomeration. However, it is generally desired that no further processing needs to be performed with the waste syrup.

The fluidized bed may have a drain rate of about 5% to about 20%. The fluidized-bed drain rate can be adjusted based on primary zone differential pressure. The lignin filter cake and the waste syrup can be fed to the fluidized bed using a dual-phase fuel feeder. The total concentration of alkali species (Na+K) and phosphorus within the fluidized bed may be held to less than 5% Sodium+Potassium+Phosphorus (Na+K+P).

Also disclosed herein are liquid material handling systems, comprising: a liquid inlet line; a steam inlet line; a water inlet line; a surge tank having a liquid inlet port fluidly connected to the liquid inlet line, a steam inlet port fluidly connected to the steam inlet line, an additive port, a recycle port, and a liquid outlet port; a heater fluidly connected to the liquid outlet port of the surge tank; and a pipe downstream of the heater which spats into (a) a feed line having a puke valve and leading to at least one feeder outlet line and (b) a return line having a pressure regulating valve and leading to both (i) the recycle port of the surge tank and (ii) storage for the liquid.

The system may further comprise a cleaning line fluidly connected to both the steam inlet line and the water inlet line. The cleaning line may also be fluidly connected to the at least one feeder outlet line. The surge tank can further comprise a mixer.

These and other non-limiting aspects of the present disclosure are discussed further herein.

BRIEF DESCRIPTION OF THE DRAWINGS

The following is a brief description of the drawings, which are presented for the purposes of illustrating embodiments disclosed herein and not for the purposes of limiting the same.

DETAILED DESCRIPTION

A more complete understanding of the components, processes, and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The singular forms "a," "an" and "the" include plural referents unless the context clearly dictates otherwise.

As used in the specification and in the claims, the term "comprising" may include the embodiments "consisting of" and "consisting essentially of" The terms "comprise(s)," "include(s)," "having," "has," "can," "contain(s)," and variants thereof, as used herein, are intended to be open-ended transitional phrases, terms, or words that require the presence of the named components/steps and permit the presence of other components/steps. However, such description should be construed as also describing compositions or processes as "consisting of" and "consisting essentially of" the enumerated components/steps, which allows the presence of only the named components/steps, and excludes other components/steps.

All ranges disclosed herein are inclusive of the recited endpoint and independently combinable (for example, the range of "from 2 watts to 10 watts" is inclusive of the endpoints, 2 watts and 10 watts, and all the intermediate values). Numerical values should be understood to include numerical values which are the same when reduced to the same number of significant figures and numerical values which differ from the stated value by less than the experimental error of conventional measurement technique of the type described in the present application to determine the value.

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression Tom about 2 to about 4" also discloses the range "from 2 to 4."

Some of the terms used herein are relative terms. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the fluids flow through an upstream component prior to flowing through a downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; upwards is always against the gravity of the earth.

To the extent that explanations of certain terminology or principles of the boiler and/or steam generator arts may be necessary to understand the present disclosure, the reader is referred to *Steam/its generation and use,* 42nd Edition, edited by G. L. Tomei, Copyright 2015, The Babcock & Wilcox Company, ISBN 978-0-9634570-2-8, the text of which is hereby incorporated by reference as though fully set forth herein.

The cellulosic ethanol biofuel production process is typically more energy intensive than the traditional starch (corn) ethanol production process. Also, the waste products from the cellulosic ethanol biofuel production process are typically not resalable as feed or fertilizer due to their chemistry. These two issues make the use of the cellulosic ethanol biofuel waste streams as a means to generate energy very attractive and potentially a significant contributor to increasing the efficiency and reducing the operating cost/production costs of a cellulosic ethanol biofuel plant. The present disclosure relates to the use of the waste stream of cellulosic ethanol biofuel production for energy generation.

Figure 4:
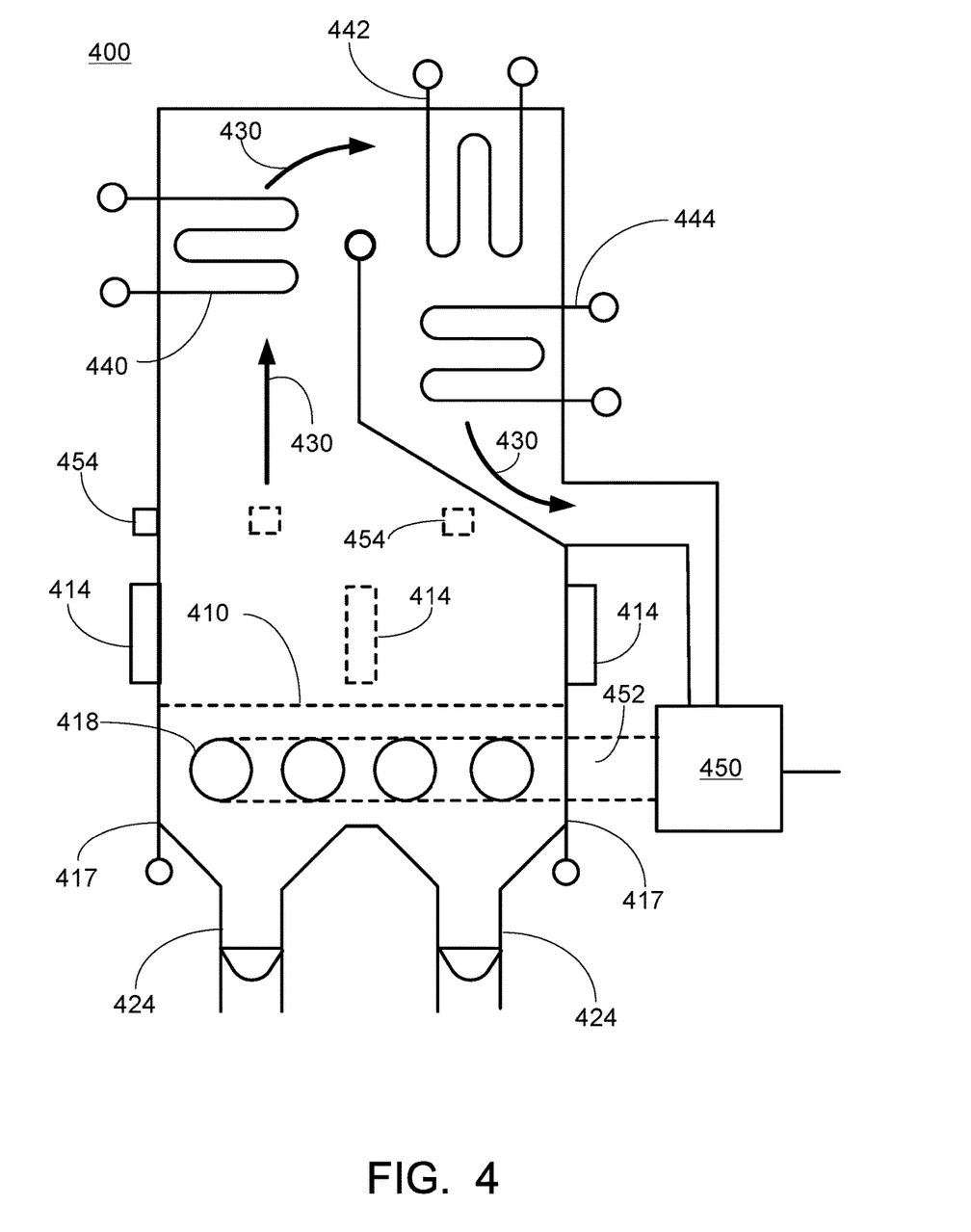
FIG. 4 is a schematic diagram of a fluidized-bed boiler illustrating some further aspects of the present disclosure.
Figure 7:
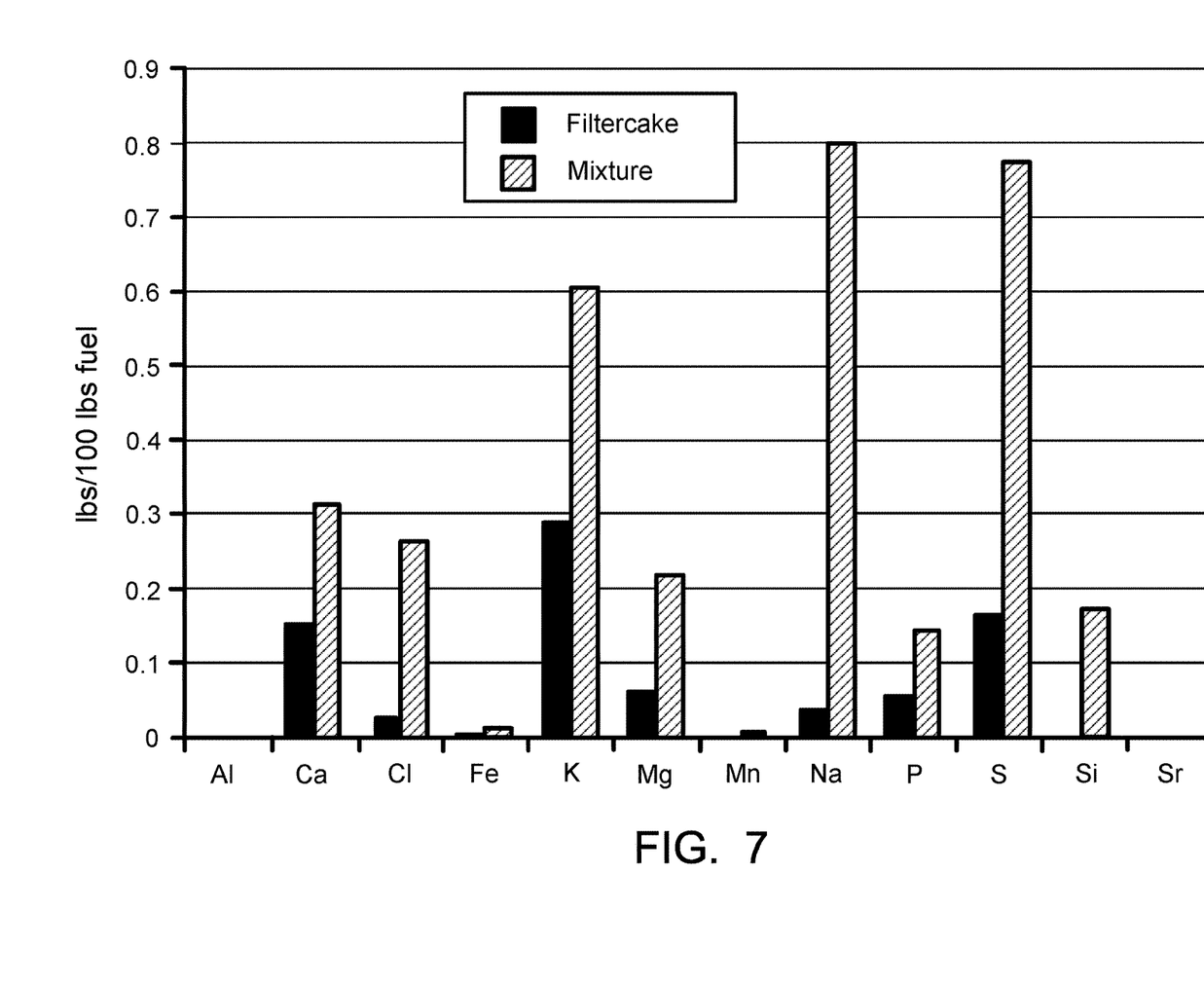
FIG. 7 is a bar graph showing the "reactive" occurrence of elements per 100 lbs fuel input.

As illustrated in FIG. 4, a fluidized-bed boiler is used for combustion of the waste products, which are the lignin filter cake and the waste syrup. When producing ethanol using cellulose as the feedstock, as compared to starch based feedstock, a unique waste is created. The cellulosic waste contains the spent chemicals, enzymes and microorganisms unique to the cellulosic process. The cellulosic process, by design, breaks down the cellulose into a usable form. The breaking down of the cellulose also increases the percentage of elements that are in a reactive form. When elements of a fuel are in a reactive form, they become available for interaction with other elements during the combustion process. Of these elements, the reactive sodium (Na), potassium (K), phosphorus (P), and sulfur (S) are the most problematic. These reactive elements are not only increasing in quantity, but are also being concentrated in the waste syrup. FIG. 7 shows the larger percentage of reactive elements present in the filter cake alone and in the mixture of filter cake and waste syrup. The large difference between the bars shows that these reactive elements are concentrated in the syrup. These results were developed using chemical fractionation as a means of analyzing the cake and waste syrup waste. It is intended that these two waste products be used in the form in which they exit the cellulosic ethanol production process. Desirably, no additional processing is needed. Again, the lignin filter cake has a moisture content of about 35% to about 60%, and is generally composed of relatively larger and more solid pieces of cellulose, hemicellulose, and lignin (compared to the syrup). The waste syrup has a moisture content of about 30% to about 50%.

The boiler can be, for example, a bubbling fluidized bed (BFB), a circulating fluidized bed (CFB), a stoker-fired boiler, or other fluidized-bed boiler. This boiler is comprised of a membrane-walled gas-tight enclose. A membrane wall design offers the advantage of a lower weight compared with a refractory-lined steel shell to achieve the same external shell temperature. A lower weight design has a lower capital cost compared with a refractory-lined shell design. The boiler includes a solid fuel feeder through which the relatively solid lignin filter cake can be introduced into the boiler. The solid fuel feeder may be a conventional solid-phase fuel feeder, or can be a dual-phase fuel feeder that is used to introduce both solid-phase lignin filter cake and liquid-phase waste syrup into the boiler.

Figure 2:
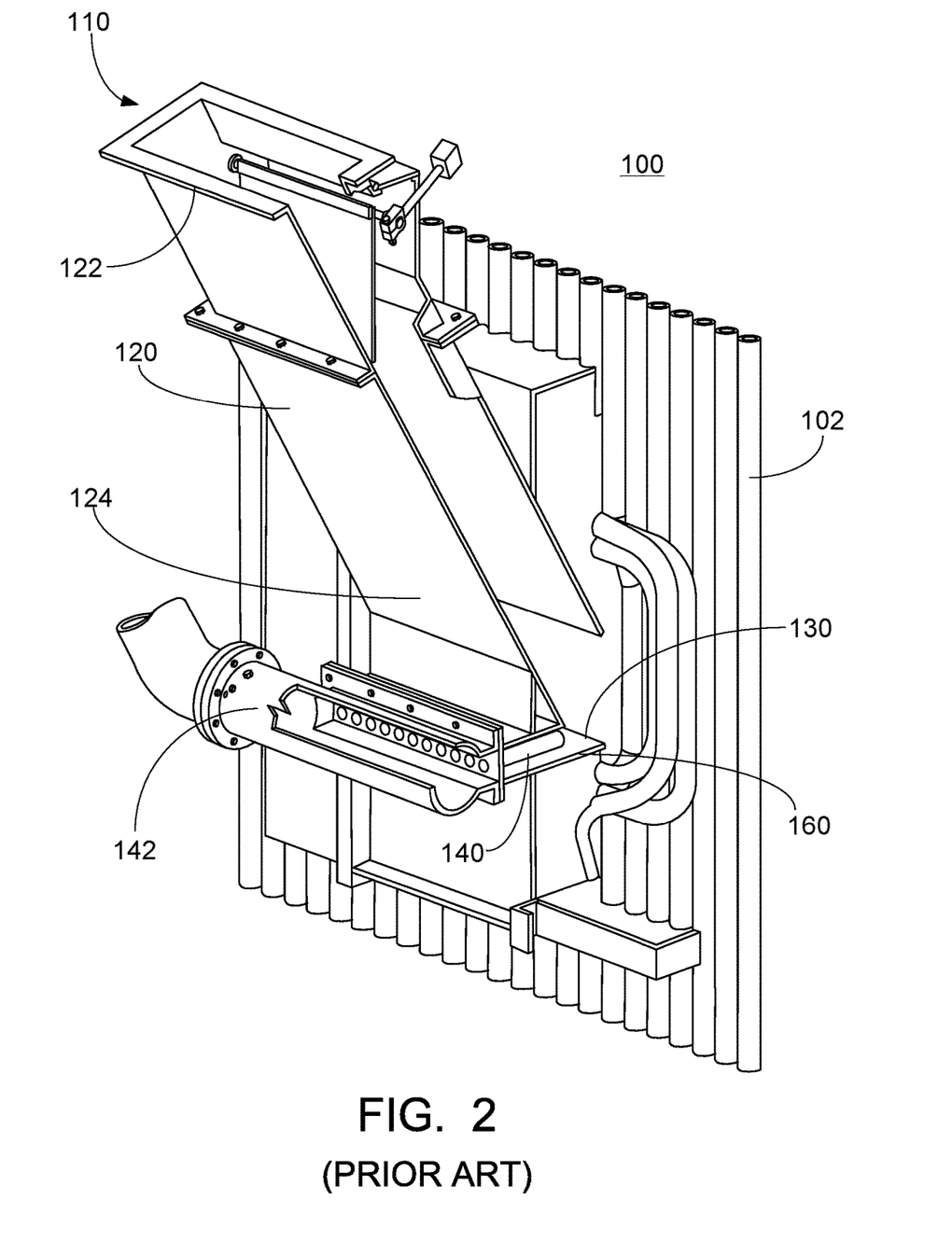
FIG. 2 is a cross-sectional perspective view of a conventional solid phase fuel feeder.

FIG. 2 shows a cross-sectional perspective illustration of a conventional solid-phase fuel feeder 110. The fuel feeder 110 is attached to the boiler located in a region generally designated by the reference number 100, and passes through a tube wall 102. Alternatively, the fuel feeder 110 may pass through a refractory (e.g. brick) furnace wall or other boiler wall. The fuel feeder 110 is designed for solid fuels only, and has a sloped chute 120. Solid fuel is fed into the top 122 of the chute and slides downwards at the bottom 124 of the chute into the boiler and contacts a plate 160. At the base 130 of the chute along the plate, gas distribution nozzles 140 are placed. These nozzles direct a gas, such as air, that propels and distributes the solid fuel off the plate and onto/into the fluidized bed (see FIG. 1, showing illustrative bed 10). The gas is provided to the distribution nozzles 140 through a gas supply pipe 142 that enters from the left side of the fuel feeder in the illustrative example. The gas could be recycled flue gas in the case of an oxy-FBC configuration. In an oxy-FBC configuration pure oxygen is supplied to the FBC in place of air for combustion.

With a fluidized-bed boiler such as the illustrative BFB boiler 8 of FIG. 1, it is desired for the fuel to be burned within the bed, not while in suspension over the bed as it is injected into the boiler by the air stream generated by the distribution nozzles 140. This is not difficult to achieve for solid fuel, which is relatively dense and will sink relatively rapidly downwards into the bed. However, with a liquid fuel or a fine particulate fuel (which acts somewhat like a gas), it can be challenging to ensure that the fuel enters the bed.

Figure 3:
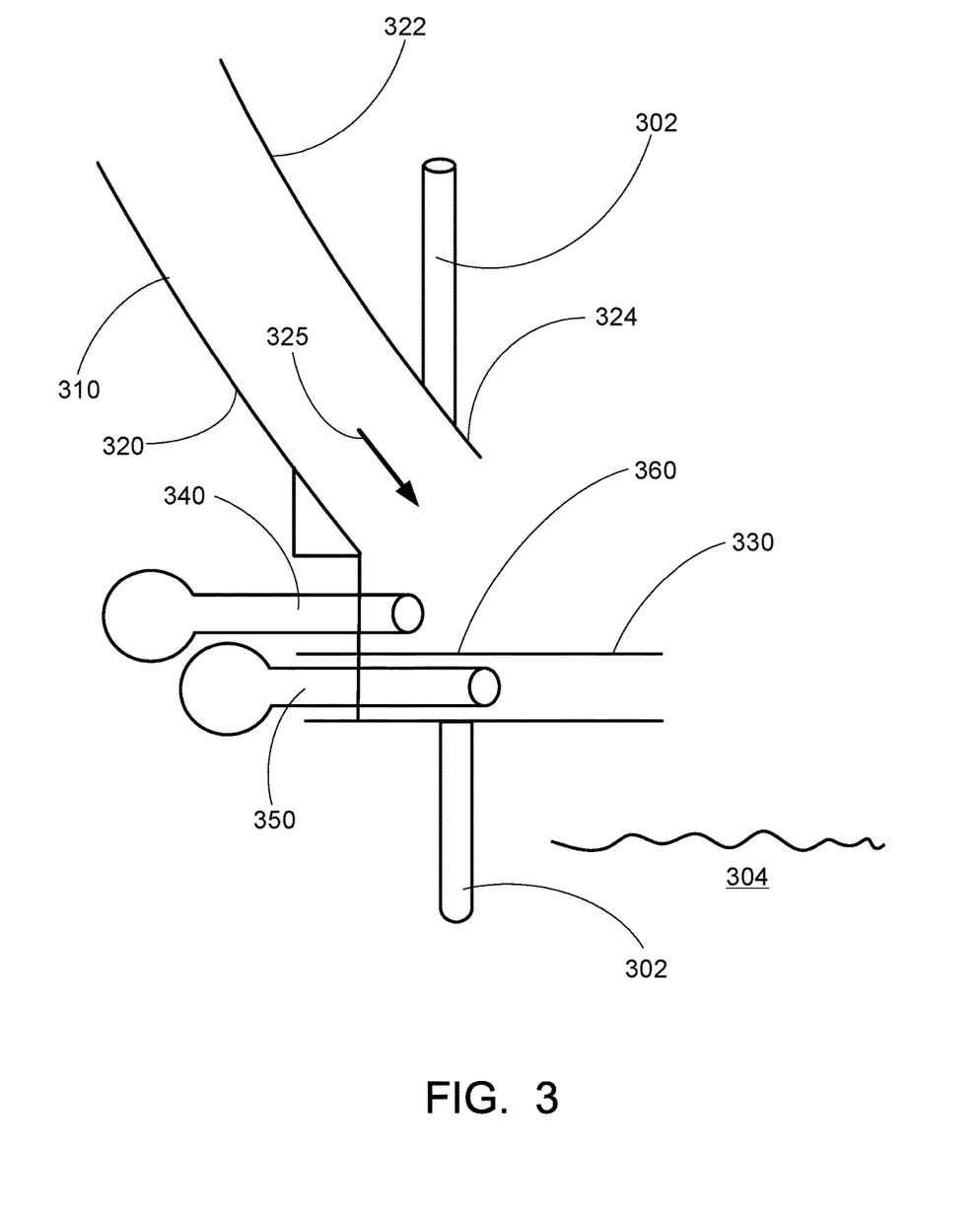
FIG. 3 is a cross-sectional perspective view of a dual-phase fuel feeder, which can be used to feed both solid fuels and liquid fuels into a fluidized-bed boiler.

FIG. 3 is a side cross-sectional view of an illustrative embodiment of a dual-phase feeder 310 which may be useful in the present disclosure. Similar to that illustrated in FIG. 2, the fuel feeder 310 passes through an opening formed in a furnace tube wall 302 which is illustrated for representational purposes with only one tube. Alternatively, the fuel feeder 310 may pass through a refractory (e.g. brick) furnace wall or other type of boiler wall. The fuel feeder 310 includes a sloped chute 320, a set of gas distribution nozzles 340, and a set of secondary nozzles 350. A plate 360 defines the base 330 of the fuel feeder 310. The sloped chute 320 has a top end 322 and a bottom end 324, the bottom end being proximate to the base 330 of the fuel feeder (i.e. plate). Solid fuel follows a solid feed path from the top end 322 to the bottom end 324 and into the boiler. The gas distribution nozzles 340 are located at the base 330 of the fuel feeder 310 and direct a gas into the solid feed path 325. The gas is usually air, though it could also be an oxygen-enriched or oxygen-depleted gas stream. The gas injected via the gas distribution nozzles 340 is used to distribute the solid fuel fed through the chute 320 across the fluidized bed 304.

Secondary nozzles 350 are also present, and direct a liquid, such as the waste syrup, into the boiler. Here, the secondary nozzles 350 are located below the base 330, so that plate 360 separates the secondary nozzles 350 from the gas distribution nozzles 340. This reduces the effect of gas injected by the gas distribution nozzles 340 on the dispersion of the liquid fuel injected by the secondary nozzles 350. and for example may be useful to reduce the potential effect of atomization of the liquid fuel by interaction with gas from the gas distribution nozzles. It is contemplated that the waste syrup can be forced through the secondary nozzles via high pressure, such that the waste syrup exits the secondary nozzles as a coherent fluid stream which is propelled to the fluidized bed 304. Other dual-phase fuel feeders are disclosed in U.S. Pat. No. 9,482,428 B2, which is hereby fully incorporated by reference in its entirety. As another alternative, the secondary nozzles 350 can be located above the sloped chute 320 or at the side of the sloped chute 320 (e.g. between adjacent sloped chutes where multiple dual-phase feeders are used), so that any solids (i.e. lignin filter cake) fed into the fluidized bed will not contact the waste syrup.

In particular, the waste syrup should be injected into the fluidized bed separately from the lignin filter cake and should not be burned in suspension. The waste syrup is desirably burned in the fluidized bed or in the freeboard (the volume between the top of the expanded fluidized bed and the convection surfaces). This is because the waste syrup exhibits a phase shift where the suspended solids enter a "plastic" phase when subjected to temperatures of above 250° F. and the moisture is driven off. The solids in the syrup appear to remain in this plastic phase through most, if not all, of the devolatilization phase. This plastic phase delays the combustion process sufficiently such that plastic phase particles, when burned in suspension, have enough time to become attached to any proximate surface or bed particles, leading to severe fouling and agglomeration. Field testing indicates that combining the waste syrup with solid fuels (e.g. lignin filter cake) above 10% did not work well.

FIG. 4 is a schematic diagram of a fluidized-bed boiler 400 that is used to illustrate some aspects of the methods of operation of the present disclosure. Initially, the boiler includes a fluidized bed 410. The fluidized bed is surrounded by water-cooled wags 417. Three fuel feeders 414 are illustrated for feeding fuel to the fluidized bed. Air ducts 418 provide the air for fluidizing the bed material, and bottom hoppers 424 are used for removing bed material for various purposes.

The fluidized bed is operated at a temperature of about 1200° F. to about 1500° F. The flue gas pathway is illustrated by dark arrows 430. Heat energy from the flue gas is captured via superheater 440, reheater 442, and economizer 444. The flue gas then passes through an air preheater 450. Flue gas exiting the boiler may be recirculated as the fluidizing medium of the fluidized bed. As illustrated here, some of the flue gas passing through air preheater 460 can be redirected to the air ducts 418 via line/pipe 452. Hue gas recirculation can be used to control the intensity of fluidization and primary zone stoichiometry while maintaining the target temperature of the fluidized bed. Flue gas has a much lower oxygen concentration compared to air, and varying the ratios of flue gas/air in the fluidizing gas allows the bed temperature and the superficial bed velocity to be controlled over a wider range. It is essential to control bed temperature in a desired range to avoid agglomeration when firing fuels high in sodium and potassium. Severe agglomeration can occur at typical fluidized-bed temperatures of 1500° F. to 1600° F. when firing cellulosic ethanol byproduct fuels. By incorporating flue gas recirculation, it is possible to maintain the desired fluidizing gas velocity to promote good mixing and combustion while optimizing the total available oxygen to moderate combustion and lower the fluidized-bed temperature below the agglomeration temperature. The balance of required air to complete combustion is introduced through secondary air ports 454.

As described, the fluidized-bed temperature can be controlled. The fluidization intensity (e.g. bubbling bed vs. circulating bed) can also be controlled. These parameters aid in controlling the rate and size of the agglomerations that are formed by the plastic phase of the waste syrup to an acceptable level that can be continuously removed with a bed material reclamation system.

Figure 5:
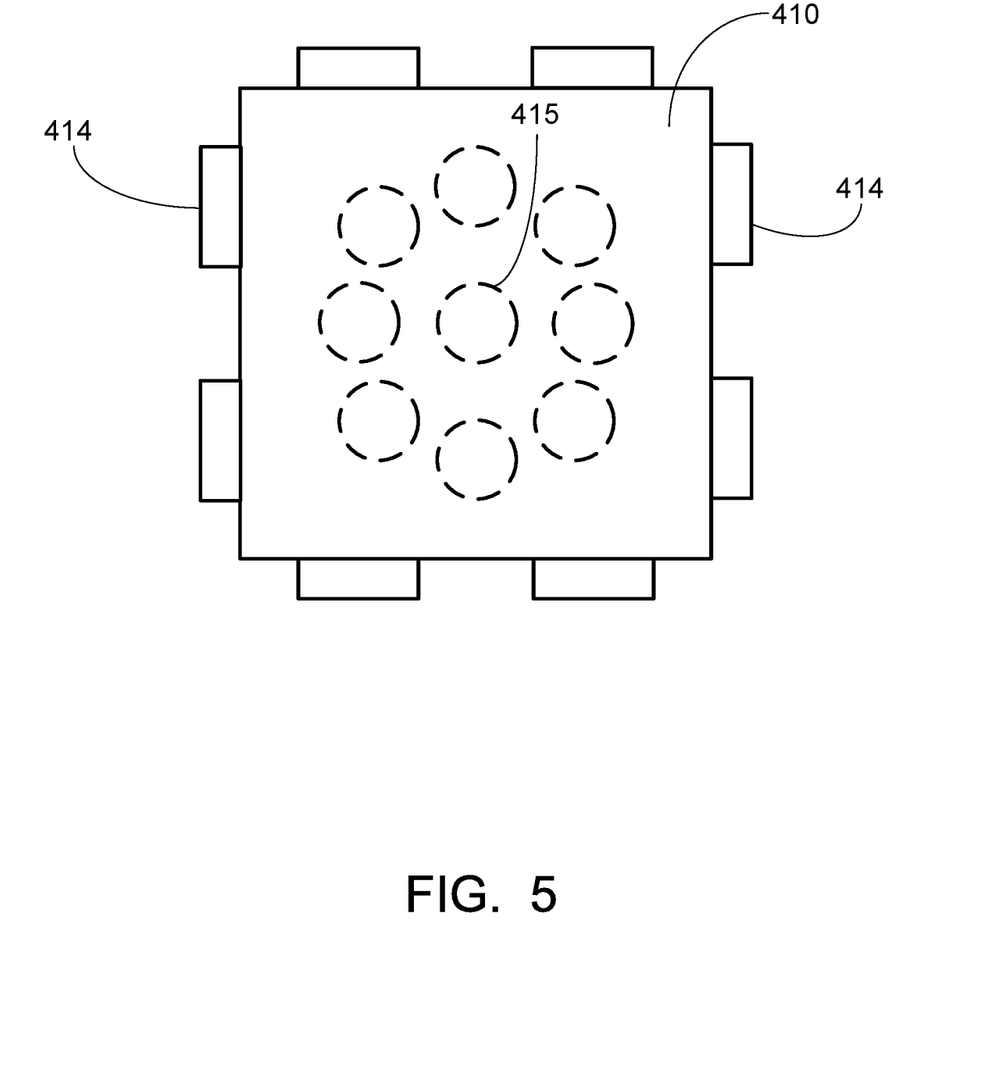
FIG. 5 is a plan view of a fluidized bed, illustrating the plan area and various locations where the waste syrup can be directed.

The waste syrup is injected into the fluidized bed as a liquid stream, with no atomization desired. The waste syrup liquid stream is directed to the plan area of the fluidized bed as a single stream or multiple streams depending on the quantity of syrup injected. FIG. 5 illustrates the placement of the waste syrup liquid streams. This is a plan view (top down) of the fluidized bed. As seen here, there are eight feeders 414 distributed about the perimeter of the fluidized bed. The target area 415 covers an area of about 10% of the plan area of the fluidized bed. It is contemplated that liquid nozzles along the walls of the boiler will be used to inject the waste syrup to the target area of the fluidized bed plan. The target area may be in the center of the plan area, i.e. surrounding the centroid. The target area does not have to be one contiguous location, but can be made up of multiple locations. For example, as illustrated here, there are nine dashed circles that make up the target area 415.

Usually, concentrating a liquid fuel in one or more locations (rather than evenly distributing the liquid fuel throughout the bed) is undesirable because the combustion chemistry can be very different compared to the rest of the bed, and because agglomeration of bed material can result. However, with the waste syrup from cellulosic ethanol production, concentration in one or more discrete locations permits the characteristic of the syrup transforming into a plastic phase to be exploited. Much of the problematic chemistry with the waste syrup (due to the spent chemicals, enzymes, micro-organism byproducts, and reactive elements) can be confined in the agglomerations formed by the plastic phase in the discrete location(s), rather than be distributed throughout the fluidized bed. The agglomerations can then be continuously removed during normal operation (e.g. via hoppers 424 illustrated in FIG. 4). Desirably, the total concentration of alkali species (Na+k) and phosphorus within the fluidized bed should be less than 5% by weight Na+K+P. An acceptable bed drain rate of 10% was demonstrated at a pilot facility to control the rate of agglomeration formation. In alternate embodiments, the commercial bed drain rate can range from about 2.5% to about 10%. The bed drain rate refers to percent of the total mass of the fluidized bed material, shown as 10 in FIG. 1, which is drained every hour.

One technique for determining the onset of agglomeration within the fluidized bed is performed using high speed primary zone differential pressure measurements. The primary zone consists of the region of the fluidized-bed boiler below the over-fire air ports as indicated by reference numeral 454 in FIG. 4. The pressure drop across the fluidized bed of solids (410 in FIG. 4) is measured with high speed pressure transducer(s). The resultant signal is analyzed to identify a deviation from a Gaussian distribution of pressure fluctuations. The bed drain rate can then be adjusted to manage agglomeration formation while minimizing the addition of fresh bed material.

If the furnace wall and heating surface temperatures are maintained below 1000° F., acceptable slagging and fouling rates are obtained. Additional absorption surfaces (such as wing walls) can be incorporated into the boiler, or the residence time of the fuel can be adjusted, to ensure adequate burnout of the fuel while inhibiting slagging and fouling.

If desired, an additive can be mixed together with the waste syrup prior to introducing the waste syrup into the boiler. The additive would raise the eutectic temperature of the ash, and reduce the agglomeration tendency of the syrup. However, this would increase operating costs and must be weighed against the cost of the bed material make-up due to agglomeration removal.

Figure 6:
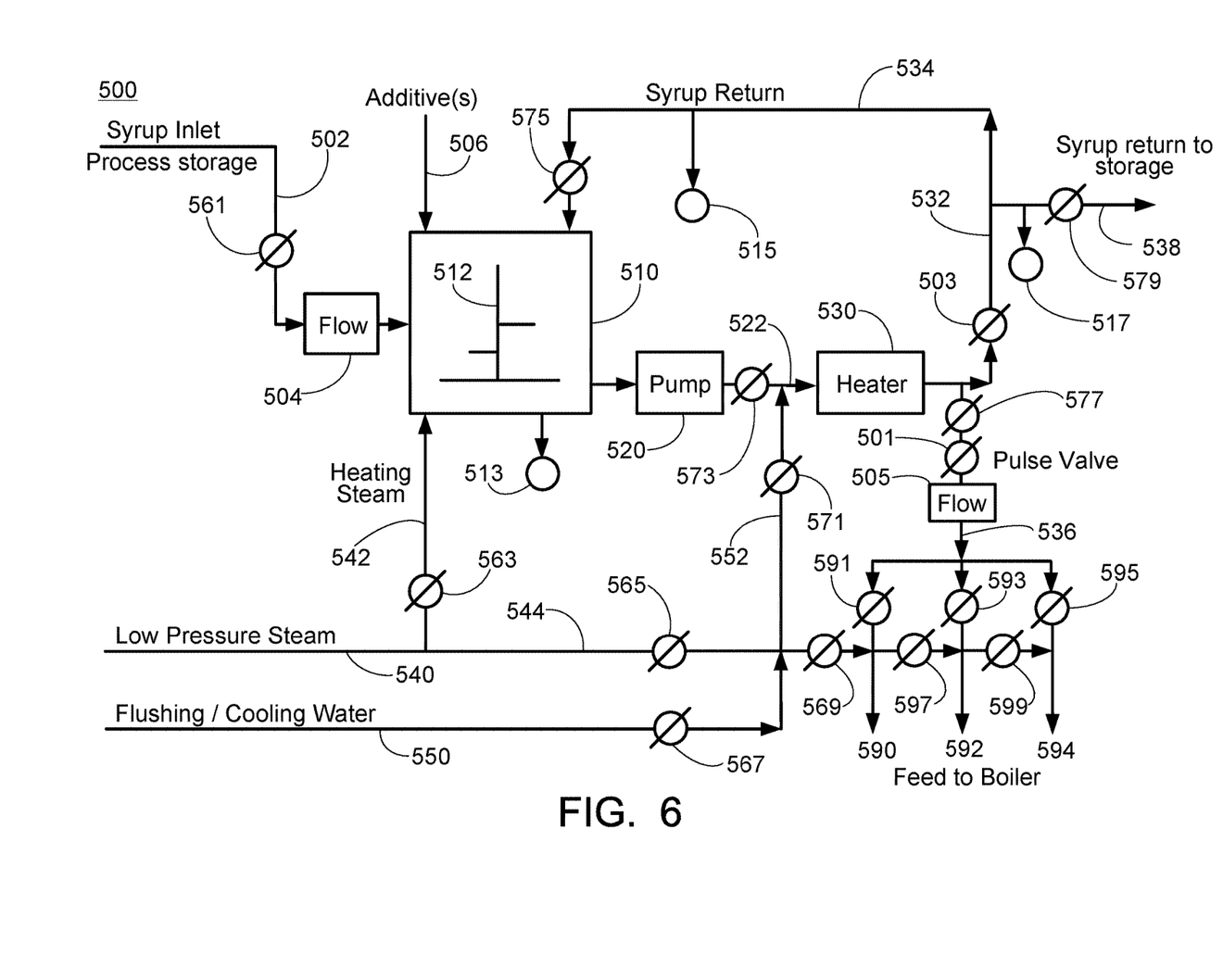
FIG. 6 is a diagram of a system for providing waste syrup to the fluidized-bed boiler.

FIG. 6 is a diagram of a system 500 that can be used to support the combustion of the waste syrup. The system regulates flow, heats the waste syrup to a desired processing temperature, keeps solids in suspension, allows for system cleaning, allows for rotation between different injection points, and allows for mixing in of additives. The system is made of corrosion resistant materials, such as stainless steel or chlorinated polyvinyl chloride (CPVC), which is both corrosion resistant and compatible with syrup preheat temperatures up to 210° F. In this regard, it is noted during testing that the waste syrup is very corrosive, and can eat through a metal storage drum in only a few weeks.

Beginning at the top left of FIG. 6, a waste syrup inlet line 502 from process storage enters the system and passes through flow meter 604 into surge tank 510. Low pressure steam enters the system through steam inlet line 540 and enters the surge tank through line/pipe 542 and heats the waste syrup to a desired temperature. The heating reduces the viscosity of the waste syrup for subsequent processing.

Due to the plastic phase occurring at about 250° F., the temperature in the surge tank should not exceed 200° F. or so, and it is contemplated that the temperature is usually about 100° F. Additive(s) 506 can also be added if desired and mixed with the syrup using mixer 512.

The waste syrup exits the surge tank 510 via pressure applied by pump 520 through line/pipe 522 and passes through heater 530, where the temperature of the syrup can be further increased if desired, although again remaining below 200° F. or so.

The waste syrup exits the heater 530 and splits into two lines, a feed line 536 and syrup return line 532. In the feed line 536, a pulse valve 501 is used to create pulses in the waste syrup flow, and the syrup then passes past flow meter 506. The waste syrup can then be flowed through any number of injection lines into the boiler, these being illustrated as feeder outlet lines 590, 592, 594 (more injection points can be present).

The syrup return line 532 splits into two different lines as well. The syrup can be sent back to storage through line/pipe 538, or can be returned to the surge tank 510 via line/pipe 534, which connects to a recycle port of the surge tank. The endpoints 590, 692, 594, 538 can be considered outlets of the waste syrup handling system.

The system includes a cleaning function as well as a means to cool out-of-service nozzles. As previously mentioned, steam enters through steam inlet line 540. A portion of the steam is routed for cleaning and cooling purposes through line 544. Water enters the system through water inlet line 550. It is noted that the water is typically cool rather than hot/warm. The steam and water can be used separately or combined into a cleaning line 552 that enters the system between the surge tank 510 and the heater 530. The cleaning fluids can then be directed to any desired location, including syrup return to storage line 538 or syrup recycle line 534. Drains 513, 515, and 517 are provided in the surge tank 610, along the syrup recycle line 634, or along the syrup return to storage line 538. The cleaning line of steam and water can also be directed to the injection points 590, 592, 594 by appropriate opening and closing of valves 569, 597, and 599.

Appropriate control systems, piping, and electrical wiring are present for controlling the waste syrup handling system 500. Several valves are illustrated in FIG. 6. Valve 561 controls the flow of syrup into the surge tank 510. Valve 563 controls the flow of steam into the surge tank 510. Valve 573 controls the flow of syrup from the surge tank into the remainder of the system.

Valve 565 controls the flow of steam passing through line/pipe 544 into the remainder of the system, and valve 567 controls the flow of water into the system. Valve 571 controls the flow of water and steam into the waste syrup upstream of the heater. Valves 577 and 503 control the flow of liquid into the injection points to the boiler, while valves 591, 593, 595 control each individual injection point. Valve 579 controls the flow of liquid back to storage, and valve 575 controls the flow of liquid into the surge tank 510. It is noted that although this system is contemplated for use with waste syrup, it could be used with any other liquid, slurry, or emulsion that can be pumped.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for generating energy from cellulosic biofuel waste, comprising:
    feeding a lignin filter cake to a fluidized bed;
    feeding a waste syrup to one or more discrete locations in the fluidized bed; and
    combusting the lignin filter cake and the waste syrup to generate energy;
    wherein the lignin filter cake does not contact the waste syrup.

2. The method of claim 1, wherein the lignin filter cake has a moisture content of about 35% to about 60%.

3. The method of claim 1, wherein the waste syrup has a moisture content of about 30% to about 50%.

4. The method of claim 1, wherein the waste syrup is fed as a stream directed at a plan area of the fluidized bed.

5. The method of claim 4, wherein the waste syrup is fed as a stream directed at a center of a plan area of the fluidized bed.

6. The method of claim 4, wherein the plan area is rectangular.

7. The method of claim 1, wherein the waste syrup is fed to the fluidized bed at a temperature of about 100° F. to about 200° F.

8. The method of claim 1, wherein the fluidized bed has a bed temperature of about 1200° F. to about 1500° F.

9. The method of claim 1, wherein flue gas generated by the fluidized bed is recirculated back to the fluidized bed.

10. The method of claim 1, wherein a furnace wall temperature is kept at about 1000° F. or less.

11. The method of claim 1, further comprising introducing an additive to the waste syrup to reduce agglomeration.

12. The method of claim 1, wherein the fluidized bed has a bed drain rate of about 2.5% to about 10%.

13. The method of claim 12, wherein the fluidized bed drain rate is adjusted based on characteristics of fluctuations in primary zone differential pressure.

14. The method of claim 1, wherein the lignin filter cake and the waste syrup are fed to the fluidized bed using a dual-phase fuel feeder.

15. The method of claim 14, wherein the waste syrup is fed below the lignin filter cake.

16. The method of claim 14, wherein the waste syrup is fed above the lignin filter cake.

17. The method of claim 14, wherein the waste syrup is fed adjacent to a filter cake feeder, or wherein the waste syrup is fed between filter cake feeders as a separate stream.

18. The method of claim 1, wherein an alkali species plus phosphorus concentration within the fluidized bed is less than 5% Na+K+P.

19. The method of claim 1, wherein water in water-cooled walls surrounding the fluidized bed flows in a closed-loop recirculation path.

20. The method of claim 1, wherein the waste syrup is combusted in the freeboard of the fluidized bed.

* * * * *